United States Patent
Ollivier

(10) Patent No.: US 7,128,890 B2
(45) Date of Patent: Oct. 31, 2006

(54) PURIFICATION OF HYDROCHLORIC ACID OBTAINED AS BY-PRODUCT IN THE SYNTHESIS OF METHANESULFONIC ACID

(75) Inventor: Jean Ollivier, Arudy (FR)

(73) Assignee: Arkema France, Puteaux (FR)

( * ) Notice: Subject to any disclaimer, the term of this patent is extended or adjusted under 35 U.S.C. 154(b) by 0 days.

(21) Appl. No.: 11/159,798

(22) Filed: Jun. 23, 2005

(65) Prior Publication Data

US 2006/0008410 A1    Jan. 12, 2006

(51) Int. Cl.
*C01B 7/07*     (2006.01)
*C07C 309/04*   (2006.01)

(52) U.S. Cl. ............ 423/488; 423/240 R; 423/243.01; 423/245.02; 562/120

(58) Field of Classification Search ............... 423/488, 423/240 R, 243.01, 245.02; 562/120, 124
See application file for complete search history.

(56) References Cited

U.S. PATENT DOCUMENTS

| | | | |
|---|---|---|---|
| 3,626,004 A * | 12/1971 | Guertin | 562/829 |
| 4,280,966 A * | 7/1981 | Hubenett | 562/829 |
| 4,549,993 A * | 10/1985 | McElligott, Jr. | 562/828 |
| 4,859,373 A * | 8/1989 | Ollivier et al. | 562/119 |
| 5,801,283 A * | 9/1998 | Ollivier et al. | 562/828 |
| 6,190,635 B1 | 2/2001 | Ollivier et al. | 423/488 |
| 6,852,883 B1 * | 2/2005 | Ollivier et al. | 562/829 |

FOREIGN PATENT DOCUMENTS

EP       894 765       3/2001

* cited by examiner

*Primary Examiner*—Ngoc-Yen Nguyen
(74) *Attorney, Agent, or Firm*—Steven D. Boyd

(57) ABSTRACT

Process for purifying the hydrochloric acid obtained as by-product in the synthesis of MSA, characterized in that the gaseous flow of hydrogen chloride evacuated from the top of the synthesis reactor is placed in contact in a treatment column, counter-currentwise, with a flow consisting of an aqueous solution of an acid chosen from methanesulfonic acid, hydrochloric acid or a mixture of these two acids, at a temperature of between 80 and 130° C.

4 Claims, 1 Drawing Sheet

Figure 1/1
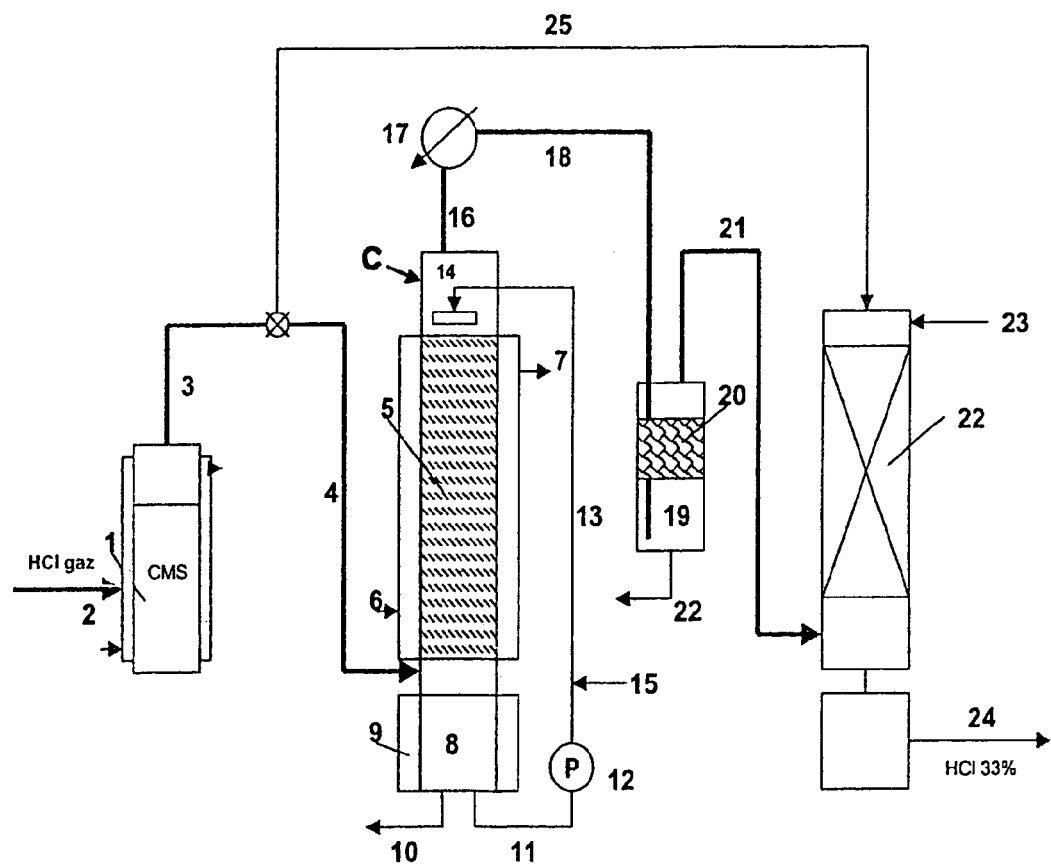

PURIFICATION OF HYDROCHLORIC ACID OBTAINED AS BY-PRODUCT IN THE SYNTHESIS OF METHANESULFONIC ACID

The present invention relates to the field of methanesulfonic acid (referred to hereinbelow as MSA) and more particularly concerns a process for purifying the hydrochloric acid obtained as by-product during the synthesis of MSA.

The synthesis of MSA from methyl mercaptan and chlorine is generally performed according to the reaction:

$$CH_3SH + 3\,Cl_2 + 3H_2O \rightarrow CH_3SO_3H + 6\,HCl$$

According to one corresponding manufacturing process, the methyl mercaptan and chlorine are introduced in gaseous form into a reactor as a homogeneous phase containing an aqueous solution of MSA, and brought to a temperature of between 90 and 110° C. The MSA produced by the reaction is evacuated in the form of an aqueous solution from the bottom of the reactor and the hydrogen chloride (in gaseous form) is evacuated from the top.

The amount of hydrogen chloride obtained as by-product via this process is very large and there is thus great interest in upgrading it financially, in particular in the form of hydrochloric acid.

However, during the reaction that leads to MSA, large amounts of a relatively volatile intermediate, methanesulfonyl chloride $CH_3SO_2Cl$ (also referred to hereinbelow as MSC) are produced in the reactor, a portion of which intermediate is entrained in the gaseous stream (or flow) of hydrogen chloride evacuated from the top of the reactor. When this gaseous flow is placed in contact with water in an absorption column in order to produce hydrochloric acid (operation known as extraction), the MSC is converted by hydrolysis into MSA, which contaminates the hydrochloric acid solution thus obtained, thereby making it unfit for a certain number of applications.

Patent application EP 894 765 (U.S. Pat. No. 6,190,635) discloses a process for purifying the hydrochloric acid obtained as by-product in the synthesis of MSA, which overcomes this drawback.

According to the said process, the excess MSC present in the gaseous flow of hydrogen chloride evacuated from the top of the reactor is, in a first stage, removed by washing the said flow, in the region of room temperature, with a flow consisting of some of the MSA produced by the reaction. However, since the gaseous stream after this first step is at a temperature in the region of 20° C., it may still contain up to about 9000 ppm of MSC, which are liable to lead, for example, to a 33% by weight hydrochloric acid solution containing from 1500 to 2500 ppm of MSA. In the present text, the percentages indicated correspond, in the absence of contrary indications, to weight percentages.

It is for this reason that EP 894 765 (U.S. Pat. No. 6,190,635) teaches a second purification step, which consists in injecting (into the gaseous flow of hydrogen chloride) an amount of water that is between 0.01% and 20% of the mass of hydrogen chloride, at a temperature of less than or equal to 15° C.

This second step has the effect of lowering the MSC content of the gaseous stream of HCl to a value which, varying according to the operating conditions, is from about 100 to 300 ppm, and at least 24 ppm.

These values are, however, liable to lead to concentrations of residual MSA or MSC in the hydrochloric acid (obtained by extraction of the gaseous stream of hydrogen chloride) that are still too high with regard to a certain number of applications, especially "food" applications, among which mention may be made of the treatments for regeneration of the resins used in water softeners.

One aim of the present invention is thus to recover the hydrogen chloride obtained as by-product in the process for manufacturing MSA, in the form of a hydrochloric acid solution having a more reduced content of MSA.

Another aim of the present invention is to further lower the content of MSC in the flow of hydrogen chloride gas leaving the reactor.

It has now been found that these aims are totally or partially achieved by the purification process according to the invention.

One subject of the present invention is thus a process for purifying the hydrochloric acid obtained as by-product in the synthesis of MSA, characterized in that the gaseous flow of hydrogen chloride evacuated from the top of the synthesis reactor is placed in contact in a treatment column, countercurrentwise, with a flow consisting of an aqueous solution of an acid chosen from methanesulfonic acid, hydrochloric acid or a mixture of these two acids, at a temperature of between 80 and 130° C.

Flows of MSA and of hydrochloric acid are readily available in the manufacturing plants performing the synthesis of MSA.

This process advantageously makes it possible to lower the MSC content of the gaseous flow of hydrogen chloride evacuated from the top of the reactor to a value of less than 0.1 ppm, which is thus very much lower than the value obtained via the process described by EP 894 765 (U.S. Pat. No. 6,190,635). This also results in the possibility of obtaining, after aqueous extraction of the said gaseous stream, a hydrochloric acid solution whose total content of residual MSA and MSC is less than 5 ppm. Furthermore, this gain in purity of the gaseous flow of hydrogen chloride is obtained via a simpler process (in only one step) than the two-step process taught by EP 894 765 (U.S. Pat. No. 6,190,635). Finally, this process makes it possible to work at a pressure in the region of atmospheric pressure, which is also very advantageous in terms of simplification.

It appears that placing the MSC in contact with the aqueous solution of MSA and/or of hydrochloric acid, at a temperature within the range indicated, allows the hydrolysis reaction of the said MSC to MSA according to:

$$CH_3SO_2Cl + H_2O \rightarrow CH_3SO_3H + HCl$$

The MSA obtained in accordance with this hydrolysis reaction is moreover separated from the gaseous stream of hydrogen chloride by entertainment in the flow of acidic aqueous solution.

The gaseous flow of hydrogen chloride is thus introduced into the bottom of the treatment column, and the flow of acidic aqueous solution is introduced into the top of this column. The acidic flow, after being placed in contact with the flow of HCl gas (and entertainment of the MSA produced by the hydrolysis), is collected at the bottom of the treatment column and returned to the top of this same column by means of a suitable circuit comprising a pump and a heat exchanger for maintaining the temperature in the range from 80 to 130° C. This circuit also comprises an inlet for injection of pure water to compensate for the consumption of water by hydrolysis of the MSC, and a purge for evacuating some of the acidic aqueous solution so as to keep the MSA content of this solution constant.

According to one preferred variant of the process according to the invention, the gaseous flow of hydrogen chloride and the flow of acidic aqueous solution are placed in contact at a temperature of between 100 and 125° C.

The acidic aqueous solution may contain variable proportions of MSA possibly ranging from 0.1% to 90% and preferably between 50% and 70%. The purge (and thus also the amount of additional water injected into the circuit mentioned above) must thus be adjusted to the desired MSA content. The purge flow rate depends on the amount of MSC brought by the HCl gas to be purified. By way of example, if 51 g/h of HCl gas are treated, containing 0.9% of MSC that is totally hydrolysed to MSA with an acidic aqueous solution containing 10% MSA, 3.85 ml/h of this solution needs to be purged in order to evacuate the 0.385 g/h of MSA formed. An equivalent amount of water is thus added.

DESCRIPTION OF FIG. 1

The laboratory device described in the attached single FIG. 1 is used. This device, designed to treat a gaseous flow of 35 litres/hour of hydrogen chloride (about 57 g/h), is made of glass with polytetrafluoroethylene (PTFE) pipes.

Pure MSC is used as fluid for saturating a flow of hydrogen chloride from a pressurized pure gas bottle. The stream (2) of HCl gas is passed through the saturator (1) containing MSC in liquid form, the said stream leaves saturated with MSC, and is conveyed via the conduits (3) and (4) to a treatment column (C) with a cross section of 26 mm, comprising two main parts:
- a heat-exchange and hydrolysis zone (5) filled with 2 mm Raschig rings to a height of 30 cm, the heat exchange taking place by means of a jacket (6 and 7) through which flows a heat-exchange fluid,
- a reboiling zone (8), which is itself provided with its own heat-exchange system comprising a heating mantle (9).

The transfer and recycling of the flow of acidic aqueous solution are performed by a circuit comprising the pump (12), the pipes (11 and 13) and the dispersion system (14) at the top of the column (C). Additional pure water is injected via the pipe (15) and purging takes place via the pipe (10).

After passing through the heat-exchange and hydrolysis zone, the gaseous flow comprising the hydrogen chloride and the entrained condensates and steam enters the conduit (16) and passes through the condenser (17). It is then directed via the conduit (18) into the separator (19).

This separator (19) is intended to retain the last possible liquid droplets entrained by the gaseous stream, which are evacuated via the conduit (22). To do this, it is equipped with a coat (20) 5 centimetres thick consisting of packed quartz wool, which is, before being installed, washed with concentrated hydrochloric acid, rinsed with distilled water and dried with anhydrous alcohol.

The hydrogen chloride gaseous stream thus purified is then conveyed via the conduit (21) into an aqueous extraction column (22). This column (22), fed with water via the conduit (23), is thermostatically regulated and operates semi-continuously to produce at (24) hydrochloric acid with a titre of 33% or 35%, depending on the need.

The same column (22) is used to control the MSC titre of the contaminated hydrogen chloride stream to be treated, doing so by circulating the HCl gaseous flow charged with MSC directly from the saturator (1) to the column (22) via the conduits (3) and (25). The MSC titre of the said stream is then calculated from the MSA titre measured after aqueous extraction in the column (22).

The examples that follow are given purely as illustrations of the invention and should not in any way be interpreted as limiting its scope.

EXAMPLE 1

Purification of an HCl Gaseous Flow Containing MSC by Placing in Contact with a Flow of an Aqueous Solution of MSA The hydrogen chloride from the pressurized pure gas bottle is diffused in the MSC saturator (1) maintained at a temperature of 18.3° C., at a flow rate of 51.5 g/h (i.e. 33.86 l/h). The HCl gaseous flow thus becomes charged with 7120 ppm of MSC vapour.

It then enters at the bottom of the treatment column (C) counter-currentwise relative to a flow of acidic aqueous solution consisting initially of 70% MSA, brought to 120° C. This aqueous flow is injected in closed circuit into the column at a flow rate of five litres/hour.

The purified gaseous flow then passes through the separator (19) and is absorbed in the water of the extraction column (22), the flow rate of which is adjusted to obtain a hydrochloric acid solution with an approximate titre of 33%.

An MSC titre of less than 0.1 ppm and an MSA titre of less than 1 ppm are measured for the hydrochloric acid solution thus obtained.

EXAMPLE 2

Purification of an HCl Gaseous Flow Containing MSC by Placing in Contact with a Flow of an Aqueous Hydrochloric Acid Solution Example 1 is repeated, replacing the acidic aqueous solution containing 70% MSA with a solution containing 20% hydrochloric acid, close to the azeotropic composition (20.22% HCl).

The temperature of the hydrolysis column is stabilized at between 105 and 110° C. (it is known that the boiling point of the water/HCl azeotrope is 108° C. at 760 torr).

The same result is obtained.

The invention claimed is:

1. A process for purifying hydrogen chloride obtained as by-product in the synthesis of methanesulfonic acid comprising:
    passing a gaseous flow of hydrogen chloride obtained from a methanesulfonic acid synthesis reactor through a treatment column, in counter-current mode, with a flow of an aqueous solution of an acid selected from the group consisting of methanesulfonic acid, hydrochloric acid and a mixture thereof, at a temperature of between 80 to 130° C. to remove methanesulfonic chloride from the hydrogen chloride flow.

2. Process according to claim 1, wherein the gaseous flow of hydrogen chloride is introduced into the bottom of the treatment column and the flow of acidic aqueous solution is introduced into the top of said column.

3. Process according to claim 1, wherein the flow of acidic aqueous solution, after being placed in contact with the flow of hydrogen chloride gas, is collected at the bottom of the treatment column and returned into the top of said columm.

4. Process according to one of claim 1, wherein the gaseous flow of hydrogen chloride and the flow of acidic aqueous solution are placed in contact at a temperature of between 100 and 125° C.

* * * * *